United States Patent [19]
Schroeppel

[11] Patent Number: 5,431,693
[45] Date of Patent: Jul. 11, 1995

[54] METHOD OF VERIFYING CAPTURE OF THE HEART BY A PACEMAKER

[75] Inventor: Edward A. Schroeppel, Lake Jackson, Tex.

[73] Assignee: Intermedics, Inc., Angleton, Tex.

[21] Appl. No.: 165,251

[22] Filed: Dec. 10, 1993

[51] Int. Cl.⁶ ............................................. A61N 1/37
[52] U.S. Cl. ........................................ 607/28; 607/26
[58] Field of Search ............................. 607/26, 27, 28

[56] References Cited

U.S. PATENT DOCUMENTS

| | | |
|---|---|---|
| 4,114,627 | 9/1976 | Lewyn . |
| 4,373,531 | 2/1983 | Wittkamph . |
| 4,537,201 | 8/1985 | Delle Vedove ............... 128/697 |
| 4,543,956 | 10/1985 | Herscovici . |
| 4,649,931 | 3/1987 | Beck . |
| 4,674,508 | 6/1987 | DeCote . |
| 4,674,509 | 6/1987 | DeCote, Jr. . |
| 4,686,988 | 8/1987 | Sholder . |
| 4,759,366 | 7/1988 | Callaghan . |
| 4,759,367 | 7/1988 | Callaghan . |
| 4,766,900 | 8/1988 | Callaghan ...................... 607/26 |
| 4,766,901 | 8/1988 | Callaghan . |
| 4,827,934 | 5/1989 | Ekwall . |
| 4,878,497 | 11/1989 | Callaghan . |
| 4,895,152 | 1/1990 | Callaghan . |
| 4,979,507 | 12/1990 | Heinz et al. . |
| 4,996,986 | 3/1991 | Thomassen . |
| 5,018,523 | 5/1991 | Bach, Jr. et al. . |
| 5,033,473 | 7/1991 | Wang et al. ..................... 128/696 |
| 5,127,401 | 7/1992 | Grevious et al. ............... 607/27 |
| 5,184,615 | 2/1993 | Nappholz et al. . |
| 5,265,603 | 11/1993 | Hurdrlik ........................ 607/61 |

Primary Examiner—William E. Kamm
Assistant Examiner—Scott M. Getzow
Attorney, Agent, or Firm—Richard L. Robinson

[57] ABSTRACT

A method of verifying cardiac capture. A cardiac signal evoked in response to a cardiac stimulation pulse is sensed via an electrode. The sensed signal is lowpass filtered to remove noise and to pass frequencies characteristic of the evoked cardiac signal. The filtered signal is processed to render a waveform signal representing the second derivative of said filtered signal and the second derivative signal is further analyzed to detect a minimum and a maximum amplitude excursion during a selected window of time beginning at a selected time delay following delivery of the cardiac stimulation pulse. The amplitude difference between the minimum and the maximum is measured and compared to a first reference value. The amplitude of the second derivative is measured during a second selected window of time beginning at a selected time delay following delivery of said cardiac stimulation pulse, and compared to a second reference value. A capture detect signal is generated if the amplitude difference exceeds the first reference value, but the amplitude does not exceed the second reference value.

10 Claims, 4 Drawing Sheets

METHOD OF VERIFYING CAPTURE OF THE HEART BY A PACEMAKER

BACKGROUND OF THE INVENTION

1. Field of the Invention

The present invention relates generally to cardiac pacing using an implantable cardiac stimulator, and more particularly to verification of capture of the heart following application of an electrical stimulating pulse by the cardiac stimulator.

2. Background Information

A cardiac stimulator, or pacemaker, "captures" the heart by delivering an electrical pulse to the myocardium of a selected chamber during an interval in the cardiac cycle in which the cardiac tissue is excitable. The electrical pulse causes depolarization of cardiac cells and a consequent contraction of the chamber, provided that the energy of the pacing pulse as delivered to the myocardium exceeds a threshold value.

It is desirable to adjust the pacemaker so that the energy delivered by the electrical pulse to the myocardium is at the lowest level that will reliably capture the heart. Such a level assures therapeutic efficacy while maximizing the life of the pacemaker battery. Because the threshold for capture varies from one implantation to another, and can change over time, it is also desirable that the pulse energy delivered by the pacemaker to the myocardium be adjustable during and subsequent to implantation. Adjustment can be effected manually from time to time through use of an external programmer that communicates with the implanted pacemaker. It would be more desirable, however, to provide a pacemaker that adjusts the pulse energy itself automatically and dynamically in response to changes in the capture threshold.

Changes in capture threshold can be detected by monitoring the efficacy of stimulating pulses at a given energy level. If capture does not occur at a particular stimulation energy level which previously was adequate to effect capture, then it can be surmised that the capture threshold has increased and that the stimulation energy level should be increased. On the other hand, if capture occurs consistently at a particular stimulation level over a relatively large number of successive stimulation cycles, it is possible that the stimulation threshold has decreased and that pacing energy is being delivered at an energy level higher than necessary. This can be verified by lowering the stimulation energy level and monitoring for loss of capture at the new energy level.

For automatic and dynamic adjustment of the stimulation energy level to be successful, it is necessary for the implantable cardiac stimulator to be able to verify that capture has occurred. Capture verification is generally accomplished by detecting an electrical potential in the heart evoked by the stimulating pulse. If capture has not occurred, there will be no evoked potential to detect. It follows that each time a stimulating pulse is delivered to the heart, the heart can be monitored during an appropriate period of time thereafter to detect the presence of the evoked potential, and thereby verify capture. In practice, however, reliable detection of the evoked potential is not a simple matter, especially where it is desired to sense the evoked potential with the same electrode that delivers the stimulating pulse. This is because the evoked potential is small in amplitude relative to the residual polarization charge on the electrode resulting from the stimulation pulse. The residual charge decays exponentially but tends to dominate the evoked potential for several hundreds of milliseconds thereafter. Several techniques for alleviating the effects of the residual charge are disclosed in the prior art.

U.S. Pat. No. 4,858,610, issued Aug. 22, 1989, to Callaghan et al., teaches the use of charge dumping following delivery of the stimulating pulse to decrease lead polarization and also the use of separate pacing and sensing electrodes to eliminate the polarization problem on the sensing electrode. U.S. Pat. No. 4,686,988, issued Aug. 18, 1987, to Sholder, teaches the use of a separate sensing electrode connected to a detector for detecting P-waves in the presence of atrial stimulation pulses, wherein the P-wave detector has an input bandpass characteristic selected to pass frequencies that are associated with P-waves. U.S. Pat. No. 4,373,531 teaches the use of pre- and post-stimulation recharge pulses to neutralize the polarization on the lead. U.S. Pat. No. 4,537,201 teaches a linearization of the exponentially decaying sensed signal by applying the sensed signal through an anti-logarithmic amplifier in order to detect a remaining nonlinear component caused by the evoked potential. U.S. Pat. No. 4,674,509, issued Jun. 23, 1987, to DeCote, Jr. teaches the generation of paired pacing pulses spaced such that at most only one pulse of each pair can induce capture. The waveforms sensed through the pacing lead following the generation of each of the pair of pulses are electronically subtracted to yield a difference signal indicative of the evoked cardiac response.

It would be desirable to provide a signal processing method for use in an implantable cardiac stimulator that permits detection of cardiac evoked potentials in the presence of a residual charge from a preceding stimulation pulse in order to verify capture of the heart, and that permits use of the same electrode to sense the evoked response as was used to deliver the stimulation pulse. This and other desirable goals are met by the present invention.

SUMMARY OF THE INVENTION

I have invented a method for discriminating between capture and non-capture signal morphologies that are sensed following delivery of the output pulse of a pacemaker. Observing that the non-capture potential is exponential in form and the evoked capture potential, while generally exponential in form, has one or more small-amplitude perturbations superimposed on the exponential waveform, the invention seeks to enhance these perturbations for ease of detection. The perturbations involve relatively abrupt slope changes, which are enhanced by processing the waveform signal by differentiation to render the second derivative of the evoked response. Abrupt slope changes in the second derivative are used to detect morphological features indicative of capture which are otherwise often difficult to discriminate. In order to eliminate detection of abrupt slope changes caused by noise, the preferred embodiment employs a lowpass filter prior to differentiation.

In accordance with one aspect of the invention, a method of verifying cardiac capture involves sensing via an electrode a cardiac signal evoked in response to a cardiac stimulation pulse. The sensed signal is filtered to remove noise. The filtered signal is processed to render a waveform signal representing the second derivative of the filtered signal. If minimum and maximum amplitude excursions of the second derivative signal occur within a selected window of time following delivery of the cardiac stimulation pulse, and if the amplitude difference between the minimum and maximum exceeds a reference value, then capture is determined to have occurred.

It is an object of the present invention to provide an improved method for discriminating non-capture and capture waveform morphologies as sensed by an intracardiac electrode following delivery of a cardiac stimulating pulse.

It is a further object of the present invention to provide an improved method for discriminating capture waveform morphologies from intrinsic contraction waveform morphologies as sensed by an intracardiac electrode following delivery of a cardiac stimulating pulse.

Other objects and advantages of the present invention will be apparent from the following description of a preferred embodiment made with reference to the drawings.

BRIEF DESCRIPTION OF THE DRAWINGS

FIGS. 3, 4 and 5 illustrate a series of waveforms showing relevant properties of first and second derivatives of sensed waveforms.

Figure 6A:
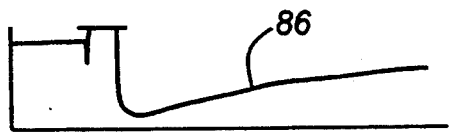
FIGS. 6 and 7 illustrate a series of waveforms showing the usefulness of the second derivative in discriminating between capture and non-capture sensed waveforms.

More particularly:

FIG. 6(a) shows a sensed waveform representative of a non-capture event.

Figure 6B:
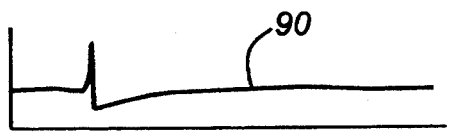

FIG. 6(b) shows the sensed waveform of FIG. 6(a) after being lowpass filtered to remove noise.

Figure 6C:
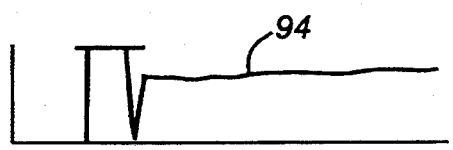

FIG. 6(c) shows the second derivative of the filtered waveform of FIG. 6(b).

Figure 7A:
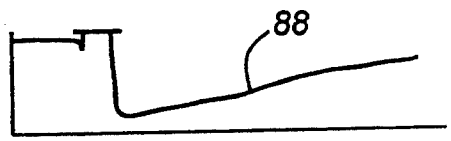

FIG. 7(a) shows a sensed waveform representative of a capture event.

Figure 7B:
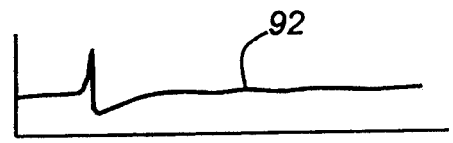

FIG. 7(b) shows the sensed waveform of FIG. 7(a) after being lowpass filtered to remove noise.

Figure 7C:
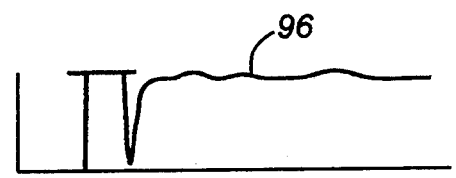

FIG. 7(c) shows the second derivative of the filtered waveform of FIG. 7(b).

Figure 8:
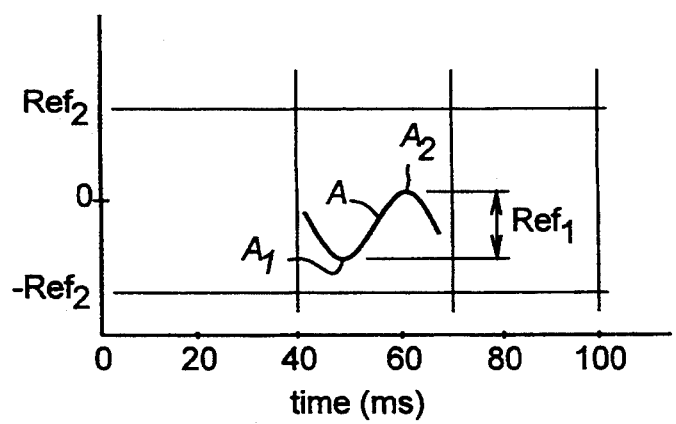

FIG. 8 illustrates a second derivative of a sensed waveform relative to certain time windows and amplitude thresholds that are useful in connection with the method of the present invention.

Figure 9:
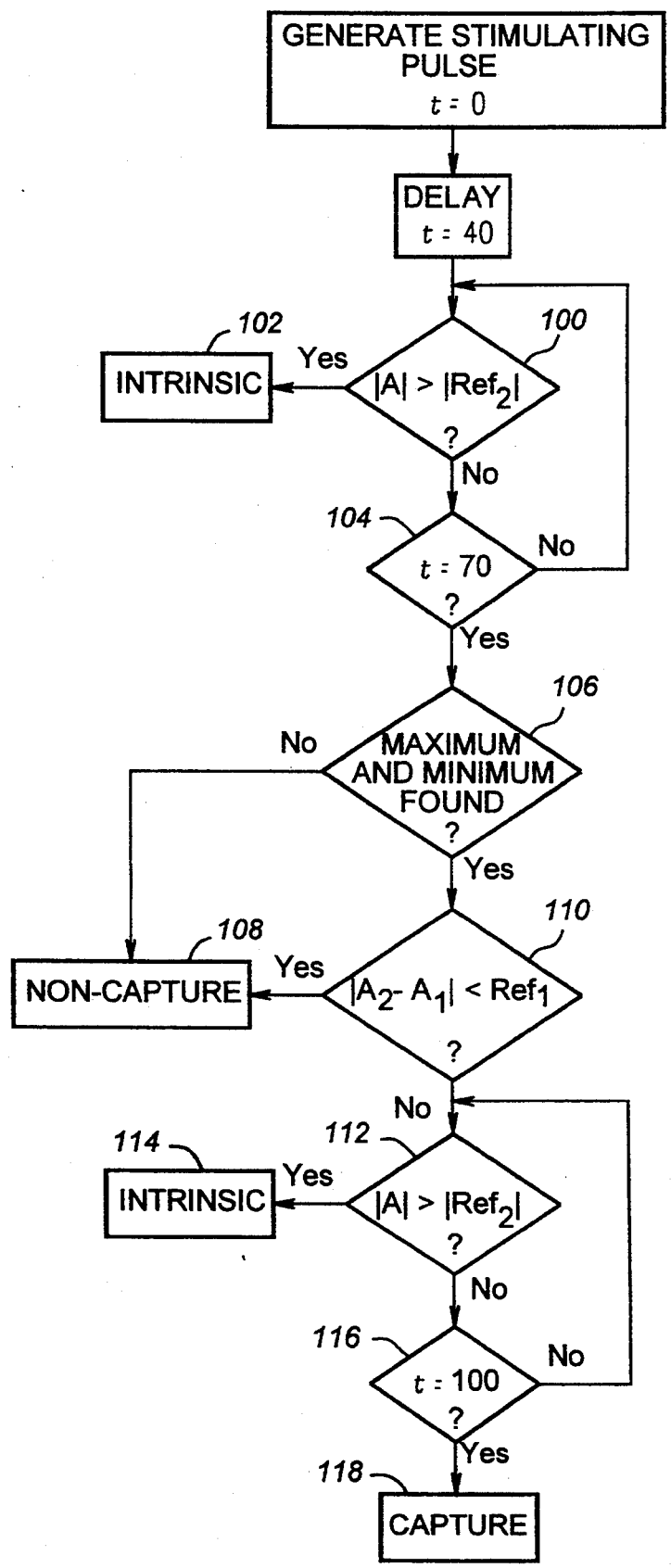

FIG. 9 is a flow chart of the method of analyzing the second derivative of a sensed waveform to detect capture of the heart in accordance with the present invention.

DETAILED DESCRIPTION OF THE PREFERRED EMBODIMENT

Figure 1:
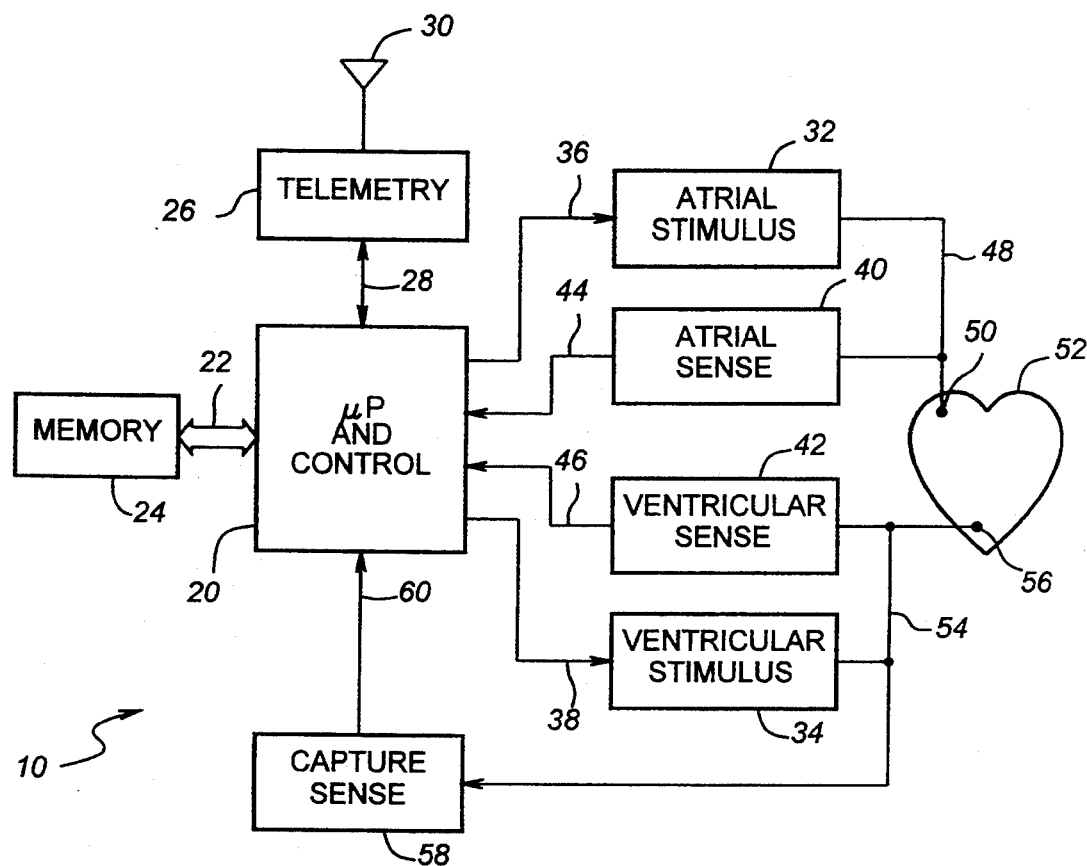
FIG. 1 is a block diagram of the preferred embodiment of a cardiac stimulator incorporating the present invention.

Referring in particular to FIG. 1, there is illustrated a block diagram of a pacemaker 10 incorporating the method of the present invention. A microprocessor and control circuit 20 preferably provides pacemaker control and means for processing digital signals. Microprocessor 20 has input/output ports connected in a conventional manner via bi-directional bus 22 to memory 24. Memory 24 preferably includes both ROM and RAM. The pacemaker operating routine is stored in ROM. The RAM stores various programmable parameters and variables.

Microprocessor 20 preferably also has an input/output port connected to a telemetry interface 26 by line 28. The pacemaker when implanted is thus able to receive pacing control parameters and variables from a transmitter of an external programmer and send data to a receiver of the external programmer if desired. Telemetry communication is preferably effected by transmission and reception, via antenna 30, of electromagnetic radiation modulated in accordance with the data to be communicated.

Microprocessor 20 also has output ports connected to inputs of an atrial stimulus pulse generator 32 and a ventricular stimulus pulse generator 34 by control lines 36 and 38, respectively. Microprocessor 20 sends pulse parameter data, such as amplitude and width, as well as enable/disable and pulse initiation codes to the generators 32 and 34 on the respective control lines 36 and 38.

Microprocessor 20 also has input ports connected to outputs of an atrial sense amplifier 40 and a ventricular sense amplifier 42 by lines 44 and 46, respectively. The atrial and ventricular sense amplifiers 40 and 42 detect occurrences of P-waves and R-waves respectively. The atrial sense amplifier 40 puts out a signal on line 44 to microprocessor 20 when a P-wave is detected. The ventricular sense amplifier 42 puts out a signal on line 46 to microprocessor 20 when an R-wave is detected.

The input of the atrial sense amplifier 40 and the output of the atrial stimulus pulse generator 32 are connected to a first conductor 48 which is connected via a conventional atrial lead to a pacing/sensing electrode 50 preferably lodged within the right atrial chamber of the heart 52.

The input of the ventricular sense amplifier 42 and the output of the ventricular stimulus pulse generator 34 are connected to a second conductor 54 which is connected via a conventional ventricular lead to a pacing/sensing electrode 56 preferably lodged within the right ventricular chamber of the heart 52.

The conductors 48 and 54 conduct the stimulus pulses generated by the atrial and ventricular stimulus pulse generators 32 and 34, respectively, to the pacing/sensing electrodes 50 and 56. The pacing/sensing electrodes 50 and 56 and corresponding conductors 48 and 54 also conduct sensed cardiac electrical signals in the right atrium and right ventricle to the atrial and ventricular sense amplifiers 40 and 42, respectively.

A capture sense signal processor 58 has an input connected to conductor 54, and an output connected via line 60 to an input port of microprocessor 20. A signal sensed in the ventricle by electrode 56 is conducted via conductor 54 to capture sense signal processor 58, where the sensed signal is processed in a manner described further below. The processed signal from capture sense signal processor 58 is conducted via line 60 to microprocessor 20 where the signal undergoes further processing and analysis in accordance with a method described below.

The present invention contemplates detecting capture of the heart by sensing via an electrode placed in the heart an electrical potential evoked in response to application of a stimulating pulse. A significant advantage of the present invention is that the same electrode that is used to deliver the stimulating pulse can also be used for detecting capture. This allows use of unipolar pacing between the lead tip and the pacer can without requiring a separate ring electrode for capture detection. Alternatively, bipolar pacing between the lead tip and ring electrode can be used without requiring a third electrode. In addition, when using bipolar pacing the tip electrode can be used as the capture detection electrode. Another advantage is that non-capture can be detected within 70 ms after delivery of the pacing pulse, which is early enough to permit a backup pacing pulse to be delivered immediately, if desired.

Figure 2:
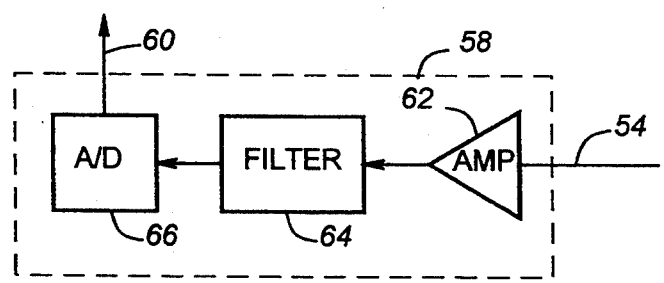
FIG. 2 is a block diagram of the capture sense block of FIG. 1, showing in greater particularity a capture sense analog signal processing circuit.

Referring to FIG. 2, the capture sense signal processor 58 of FIG. 1 is illustrated in greater detail. In the preferred embodiment, signal processor 58 includes a pre-amplifier 62 having an input to which sensed electrical activity signals from the heart are applied. The input of pre-amplifier 62 is electrically connected via conductor 54 of an endocardial lead to the tip electrode 56 located in the right ventricle of the heart. The signal from tip electrode 56 is sensed relative to a second electrode, preferably an external conductive surface of the pacemaker housing or "can," in a unipolar pacing configuration. Nevertheless, it should be understood that the input to pre-amplifier 62 can also be connected to a ring electrode. Alternatively, the input to pre-amplifier 62 can be connected to the tip electrode 56 with the signal being sensed relative to a ring electrode in a bipolar pacing configuration. Finally, it should be appreciated that capture sense signal processor 58, while shown connected to an electrode within a ventricle, could be connected instead to an electrode within an atrium of the heart.

The amplified output signal of pre-amplifier 62 is applied to the input of a following lowpass filter stage 64 having a cutoff frequency of about 50 Hz. Lowpass filter stage 64 is employed to remove high frequency noise that is not indicative of capture but that might cause false detection of capture.

The filtered output of filter stage 64 is applied to the input of a following analog to digital converter stage 66 in which the amplified and filtered analog signal is digitized for further processing by microprocessor 20 in accordance with the capture detection method described below.

Figure 3A:
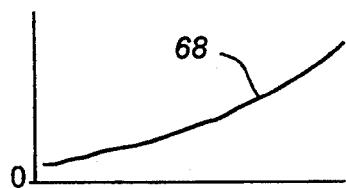
FIG. 3(a) shows a hypothetical evoked response morphology.
Figure 4A:
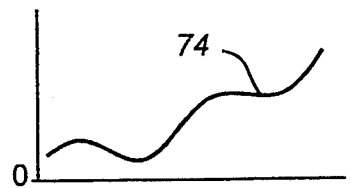
FIG. 4(a) shows another hypothetical evoked response morphology.
Figure 5A:
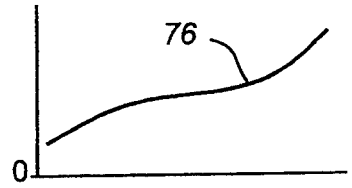
FIG. 5(a) shows yet another hypothetical evoked response morphology.
Figure 3B:
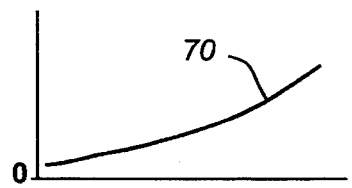
FIG. 3(b) shows the first derivative of the morphology of FIG. 3(a).
Figure 4B:
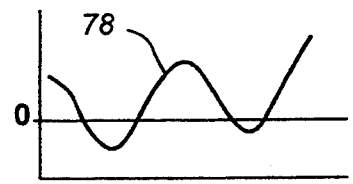
FIG. 4(b) shows the first derivative of the morphology of FIG. 4(a).
Figure 5B:
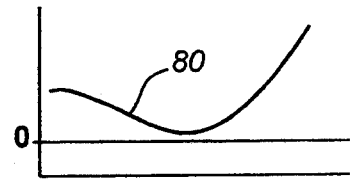
FIG. 5(b) shows the first derivative of the morphology of FIG. 5(a).
Figure 3C:
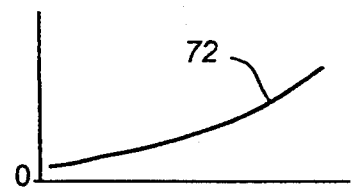
FIG. 3(c) shows the second derivative of the morphology of FIG. 3(a).
Figure 4C:
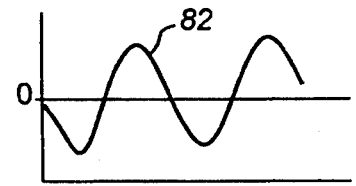
FIG. 4(c) shows the second derivative of the morphology of FIG. 4(a).
Figure 5C:
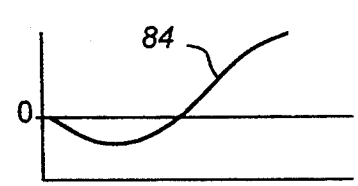
FIG. 5(c) shows the second derivative of the morphology of FIG. 5(a).

FIGS. 3, 4 and 5 illustrate some general properties of the derivatives of evoked response morphologies. More particularly, FIGS. 3(a), 4(a) and 5(a) show hypothetical evoked response morphologies. FIGS. 3(b), 4(b) and 5(b) show the first derivatives of the morphologies of FIGS. 3(a), 4(a) and 5(a), respectively. FIGS. 3(c), 4(c) and 5(c) show the second derivatives of the morphologies of FIGS. 3(a), 4(a) and 5(a), respectively. An exponential, or nearly exponential, waveform 68 has a first derivative 70 and a second derivative 72 that are smooth and exponential, or nearly exponential. Exponential waveforms 74 and 76, with perturbations, have first derivatives 78 and 80, respectively, which exaggerate the perturbations. The first derivative waveforms may or may not cross zero as illustrated by waveforms 78 and 80, respectively. Second derivative waveforms 82 and 84 further emphasize the perturbations and cross zero as the slope of the first derivative reaches an inflection point.

FIGS. 6 and 7 illustrate the power of the method of the present invention for discriminating an evoked response waveform indicative of capture from a non-capture waveform. FIGS. 6(a) and 7(a) show sensed waveforms representative of non-capture and capture events, respectively. FIGS. 6(b) and 7(b) show the sensed waveforms after being lowpass filtered to remove noise. FIGS. 6(c) and 7(c) show the second derivatives of the filtered waveforms.

A four volt, 1 millisecond wide unipolar pulse was delivered to the heart between a tip electrode of a lead and the pacemaker case. The resultant waveform was sensed between the tip and case. The task is to discriminate the non-capture morphology 86 from the capture morphology 88. Waveforms 86 and 88 correspond to typical input waveforms to the capture sense signal processor 58 of FIG. 1. The output waveforms 90, 92 of lowpass filter 64 as shown in FIGS. 6(b) and 7(b) are difficult to discriminate. The second derivatives 94, 96 generated in accordance with the method of the present invention clearly develop the perturbations in the capture morphology, whereas the non-capture morphology remains relatively featureless.

Referring to FIGS. 8 and 9, the method of the present invention is illustrated. It should be understood that the filtered and digitized signal from capture sense signal processor 58 is analyzed by microprocessor 20 in accordance with the procedure illustrated in FIG. 9, including the prior step of differentiating the digitized sensed waveform to render the second derivative. FIG. 8 shows a portion of the second derivative waveform having a varying amplitue A as viewed within a first window of time from about 40 msec to about 70 msec after delivery of the stimulating pulse. If both a minimum peak A1 and a maximum peak A2 are not found by the end of the 40 to 70 msec window of time, the stimulating pulse is classified as not having captured the heart, provided that the absolute value of the amplitude A has not exceeded the absolute value of an empirically determined threshold value $Ref_2$, such as 0.00005 V/sec$^2$, or $-Ref_2$, such as $-0.00005$ V/sec$^2$, within that first window of time. If at least one minimum peak A1 and one maximum peak A2 (which may occur in either order) are found within the 40 to 70 msec window, but the peak-to-peak amplitude difference between A1 and A2 is less than an empirically determined threshold value $Ref_1$, such as 0.00001 V/sec$^2$ for instance, the stimulating pulse is also classified as not having captured the heart, provided that the absolute value of the amplitude has not exceeded the absolute value of threshold value $Ref_2$. If the peak-to-peak amplitude difference between A1 and A2 is equal to or greater than the threshold value $Ref_1$, it is tentatively determined that capture has occurred, although it is possible that the peak-to-peak excursion has exceeded the first threshold value $Ref_1$ not due to an evoked response indicative of capture, but due to the occurrence of an intrinsic contraction manifested within the first window of time. Signals generated by intrinsic contractions tend to be of significantly greater magnitude than evoked responses indicative of capture. The method measures the amplitude A of the second derivative over an extended window of time, i.e., from about 40 ms to about 100 ms after delivery of the stimulating pulse, to identify intrinsic contractions. If the absolute value of the amplitude A exceeds the absolute value of the second threshold value $Ref_2$ within the extended window of time, it is determined that an intrinsic contraction has occurred. If the absolute value of the amplitude A does not exceed the absolute value of the second threshold $Ref_2$ at any time during the extended window of time from about 40 ms to about 100 ms, and if the peak-to-peak amplitude difference has exceeded the first threshold $Ref_1$ during the first window of time from about 40 ms to about 70 ms, it is determined that capture has occurred.

Referring in particular to FIG. 9, the method of the present invention is described in greater detail with respect to the analysis of the second derivative of the sensed waveform performed by microprocessor 20, with the second derivative also being rendered by microprocessor 20. Starting at a selected delay of about 40 ms after delivery of the stimulating pulse, the method compares the absolute value of the waveform amplitude A to the absolute value of a reference value $Ref_2$, as indicated by decision box 100. If the absolute value of the amplitude A exceeds the absolute value of $Ref_2$, it is determined that an intrinsic contraction has occurred, as indicated by box 102. If the absolute value of the amplitude A does not exceed the absolute value of $Ref_2$, the comparison is repeated until either the absolute value of the amplitude A exceeds $Ref_2$ or time $t=70$ ms is reached, as indicated by decision box 104. Alternatively, positive and negative amplitude peaks $A_2$ and $A_1$ can be compared to corresponding positive and negative reference values $Ref_2$ and $-Ref_2$ rather than comparing the absolute value of the amplitude A to the absolute value of $Ref_2$.

At time $t=70$, if the waveform has not previously been classified as an intrinsic contraction, the method determines whether an amplitude maximum and minimum have been found during the interval from $t=40$ to $t=70$, as indicated by decision box 106. If both maximum and minimum peaks have not been found, it is determined that capture has not occurred, as indicated by box 108. If both maximum and minimum amplitude peaks have been found, the method determines whether the absolute value of the amplitude difference between the maximum and minimum amplitude peaks is less than a reference value $Ref_1$, as indicated by decision box 110. If the amplitude difference is less than $Ref_1$, then it is determined that capture has not occurred, as indicated by box 108. If the amplitude difference is equal to or exceeds $Ref_1$, the method determines whether the absolute value of the waveform amplitude A exceeds the absolute value of $Ref_2$, as indicated by decision box 112. If the absolute value of $Ref_2$ is exceeded, it is determined that the waveform is the result of an intrinsic contraction, rather than a capture, as indicated by box 114. If the absolute value of the waveform amplitude A is equal to or less than the absolute value of $Ref_2$, then the method continues to compare the absolute value of the amplitude to the absolute value of $Ref_2$ until either the absolute value of $Ref_2$ is exceeded or $t=100$ ms, as indicated by decision box 116. If $t=100$ ms without the absolute value of $Ref_2$ having been exceeded during the period $t=70$ to $t=100$, then it is determined that a capture occurred, as indicated by box 118.

In the event that application of the method described above and illustrated in FIG. 9 results in a determination of non-capture as of the end of the first window of time at $t=70$, as indicated by box 108, it may nevertheless be useful to continue to look for intrinsic contractions that are manifested within that portion of the extended window of time from $t=70$ to $t=100$ ms. This can be accomplished by comparing the absolute value of the waveform amplitude A to the absolute value of $Ref_2$ from $t=70$ to $t=100$. If the absolute value of $Ref_2$ is exceeded during that time period, it will be determined that a non-capture was followed by an intrinsic contraction.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims. It should further be appreciated that while the method of the present invention has been disclosed as being implemented with a microprocessor, it is also possible to implement the method utilizing a combination of analog circuits and hardwired digital logic.

What is claimed is:

1. A method of detecting cardiac non-capture by sensing via an electrode a cardiac signal after delivery of a cardiac stimulation pulse, comprising the steps of:
   sensing a waveform signal at said electrode following delivery of said cardiac stimulation pulse;
   filtering said sensed waveform signal to pass frequencies characteristic of an evoked cardiac capture signal;
   processing said filtered waveform signal to render a second derivative waveform signal representing the second derivative of said filtered signal;
   processing and analyzing said second derivative waveform signal to detect a minimum and a maximum amplitude excursion during a selected window of time beginning at a selected time delay following delivery of said cardiac stimulation pulse; and
   measuring the amplitude difference between said minimum and said maximum, and comparing said amplitude difference to a reference value and generating a non-capture detect signal if said amplitude difference does not exceed said reference value.

2. The method of claim 1, in which said selected window of time comprises a first selected window of time, and further including the steps of:
   measuring the amplitude of said second derivative waveform signal during a second selected window of time beginning at a selected time delay following delivery of said cardiac stimulation pulse;
   comparing said amplitude to a second reference value, and generating an intrinsic contraction detect signal if said amplitude exceeds said second reference value during said second selected window of time; and not generating said non-capture detect signal if said amplitude exceeds said second reference value during said second selected window of time.

3. The method of claim 2, in which said second window of time ends at a time later than said first window of time.

4. A method of detecting cardiac capture by sensing via an electrode a cardiac signal after delivery of a cardiac stimulation pulse, comprising the steps of:
   sensing a waveform signal at said electrode following delivery of said cardiac stimulation pulse;
   filtering said sensed waveform signal to pass frequencies characteristic of an evoked cardiac capture signal;
   processing said filtered waveform signal to render a second derivative waveform signal representing the second derivative of said filtered signal;
   processing and analyzing said second derivative waveform signal to detect a minimum and a maximum amplitude excursion during a selected window of time beginning at a selected time delay following delivery of said cardiac stimulation pulse; and
   measuring the amplitude difference between said minimum and said maximum, and comparing said amplitude difference to a reference value and generating a capture detect signal if said amplitude difference exceeds said reference value.

5. The method of claim 4, in which said selected window of time comprises a first selected window of time and said reference value comprises a first reference value, and further including the steps of:
   measuring the amplitude of said second derivative waveform signal during a second selected window of time beginning at a selected time delay following delivery of said cardiac stimulation pulse;
   comparing said amplitude to a second reference value, and generating an intrinsic contraction detect signal if said amplitude exceeds said second reference value during said second selected window of time; and
   not generating said capture detect signal if said amplitude exceeds said second reference value during said second selected window of time.

6. The method of claim 5, in which said second window of time ends at a time later than said first window of time.

7. A method of discriminating between a cardiac capture and an intrinsic contraction by sensing via an electrode a cardiac signal after delivery of a cardiac stimulation pulse, comprising the steps of:
   sensing a waveform signal at said electrode following delivery of said cardiac stimulation pulse;
   filtering said sensed waveform signal to pass frequencies characteristic of an evoked cardiac capture signal;
   processing said filtered waveform signal to render a waveform signal representing the second derivative of said filtered signal;
   processing and analyzing said second derivative waveform signal to detect a minimum and a maximum amplitude excursion during a first selected window of time beginning at a selected time delay following delivery of said cardiac stimulation pulse;
   measuring the amplitude difference between said minimum and said maximum, and comparing said amplitude difference to a first reference value;
   measuring the amplitude of said second derivative waveform signal during a second selected window of time beginning at a selected time delay following delivery of said cardiac stimulation pulse; and
   comparing said amplitude difference to a first reference value, and comparing said amplitude to a second reference value, and generating a capture detect signal if said amplitude difference exceeds said first reference value, but said amplitude does not exceed said second reference value.

8. The method of claim 7, in which said second reference value is greater than said first reference value.

9. The method of claim 8, in which said second window of time ends at a time later than said first window of time.

10. A method of detecting an intrinsic contraction by sensing via an electrode a cardiac signal after delivery of a cardiac stimulation pulse, comprising the steps of:
    sensing a waveform signal at said electrode after delivery of said cardiac stimulation pulse;
    processing said sensed waveform signal to render a second derivative waveform signal representing the second derivative of said sense waveform signal;
    measuring the amplitude of said second derivative waveform signal during a selected window of time beginning at a selected time delay following delivery of said cardiac stimulation pulse; and
    comparing said amplitude to a reference value, and generating an intrinsic contraction detect signal if said amplitude exceeds said reference value during said selected window of time.

* * * * *